United States Patent
Stephens

(10) Patent No.: US 10,098,341 B2
(45) Date of Patent: Oct. 16, 2018

(54) FREEZE STABLE TETRAKIS(HYDROXYMETHYL) PHOSPHONIUM SULFATE FORMULATIONS

(71) Applicant: Rohm and Haas Company, Collegeville, PA (US)

(72) Inventor: Randall W. Stephens, Perkasie, PA (US)

(73) Assignee: ROHM AND HAAS COMPANY, Collegeville, PA (US)

( * ) Notice: Subject to any disclaimer, the term of this patent is extended or adjusted under 35 U.S.C. 154(b) by 0 days.

(21) Appl. No.: 15/556,760

(22) PCT Filed: Mar. 15, 2016

(86) PCT No.: PCT/US2016/022412
§ 371 (c)(1),
(2) Date: Sep. 8, 2017

(87) PCT Pub. No.: WO2016/149236
PCT Pub. Date: Sep. 22, 2016

(65) Prior Publication Data
US 2018/0042222 A1 Feb. 15, 2018

Related U.S. Application Data

(60) Provisional application No. 62/134,798, filed on Mar. 18, 2015.

(51) Int. Cl.
*A01N 25/02* (2006.01)
*A01N 57/34* (2006.01)

(52) U.S. Cl.
CPC ............ *A01N 25/02* (2013.01); *A01N 57/34* (2013.01)

(58) Field of Classification Search
CPC ..................................................... A01N 25/02
See application file for complete search history.

(56) References Cited

FOREIGN PATENT DOCUMENTS

| WO | 2011/076798 A1 | | 6/2011 | |
|---|---|---|---|---|
| WO | WO 2011/076798 | * | 6/2011 | ............... C07F 9/54 |
| WO | 2014/025994 A1 | | 2/2014 | |
| WO | 2015/017705 A1 | | 2/2015 | |

OTHER PUBLICATIONS

Vallat Machine Translation (Year: 2011).*
Xu et al (in "Microbial pathogens and strategies for combating them: science, technology and education" (A. Mendez-Vilas, Ed), 2013) (Year: 2013).*
AQUCAR® MSDS (online at http://msdssearch.dow.com/PublishedLiteratureDOWCOM/dh_030b/0901b8038030b48f.pdf?filepath=biocides/pdfs/noreg/253-01944.pdf, accessed Feb. 7, 2018) (Year: 2018).*

* cited by examiner

*Primary Examiner* — Craig D Ricci
(74) *Attorney, Agent, or Firm* — Tifani M. Edwards

(57) ABSTRACT

A composition comprising:
(a) tetrakis(hydroxymethyl)phosphonium sulfate (THPS); (b) water; and (c) methanol; wherein the weight percentages of (a), (b) and (c) are within the area on a ternary phase diagram for (a), (b) and (c) bounded by four points: (A) 5% THPS/58% water/37% methanol; (B) 5% THPS/36% water/59% methanol; (C) 65% THPS/27% water/8% methanol; and (D) 65% THPS/29% water/6% methanol.

4 Claims, 4 Drawing Sheets

FREEZE STABLE TETRAKIS(HYDROXYMETHYL) PHOSPHONIUM SULFATE FORMULATIONS

This invention relates to formulations of tetrakis(hydroxymethyl)phosphonium sulfate (THPS) which do not freeze when stored at low temperatures.

Formulations of biocidal active ingredients often are stored or used under conditions including extremely low temperatures, including, e.g., oil and gas extraction. Compositions containing THPS and various solvents have been reported in the literature, but compositions which are stable at low temperatures are not known. For example, WO2015/017705 discloses compositions containing THPS and various solvents, but this reference does not suggest the compositions claimed herein.

STATEMENT OF THE INVENTION

The present invention is directed to a composition comprising:
(a) tetrakis(hydroxymethyl)phosphonium sulfate (THPS); (b) water; and (c) methanol; wherein the weight percentages of (a), (b) and (c) are within the area on a ternary phase diagram for (a), (b) and (c) bounded by four points: (A) 5% THPS/58% water/37% methanol; (B) 5% THPS/36% water/59% methanol; (C) 65% THPS/27% water/8% methanol; and (D) 65% THPS/29% water/6% methanol.

The present invention is further directed to a composition comprising about 50% THPS/28% water/22% methanol.

DETAILED DESCRIPTION OF THE INVENTION

Figure 1:
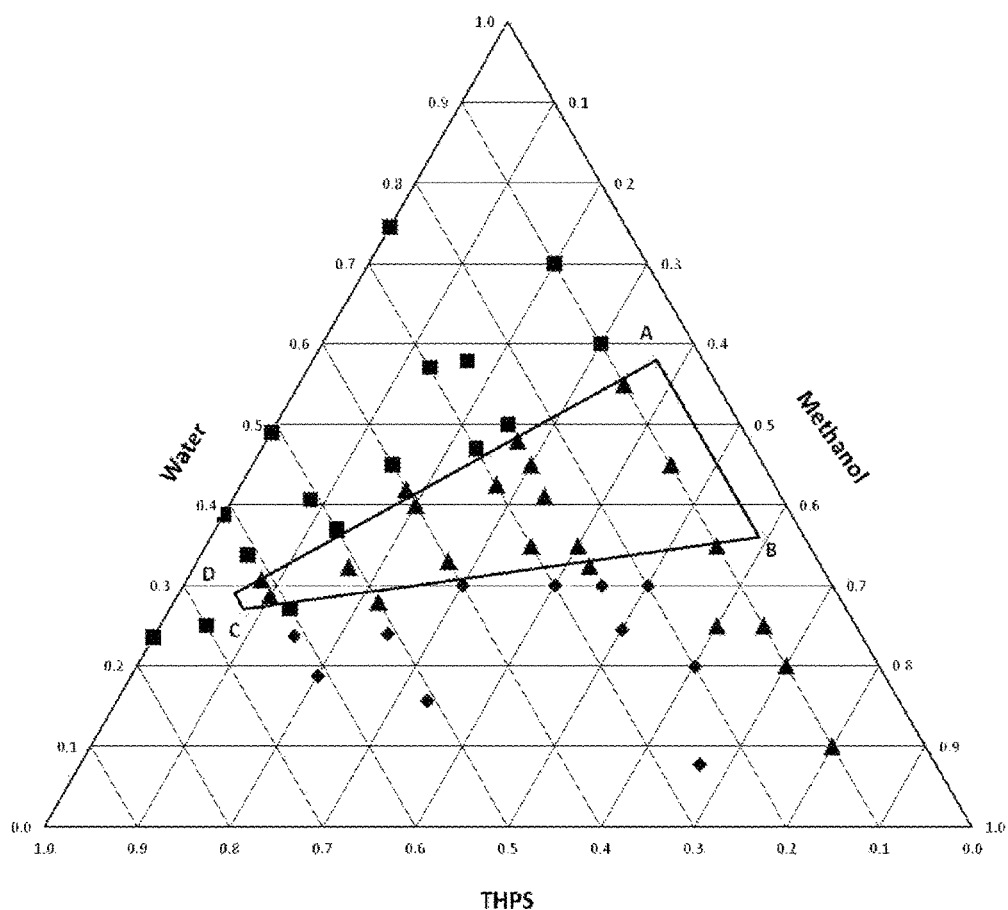
FIG. 1 is a ternary phase diagram for THPS/water/methanol, with the claimed area marked by the points A, B, C and D, which are the vertices of a quadrilateral. The symbol "▲" indicates a point for which the mixture of that composition is a free-flowing single liquid phase after 24 hour storage at −40° C. The symbol "■" indicates a point for which the mixture is solid under these conditions and "♦" indicates a point for which the mixture contains either both liquid and solid or two liquid phases under these conditions.
Figure 2:
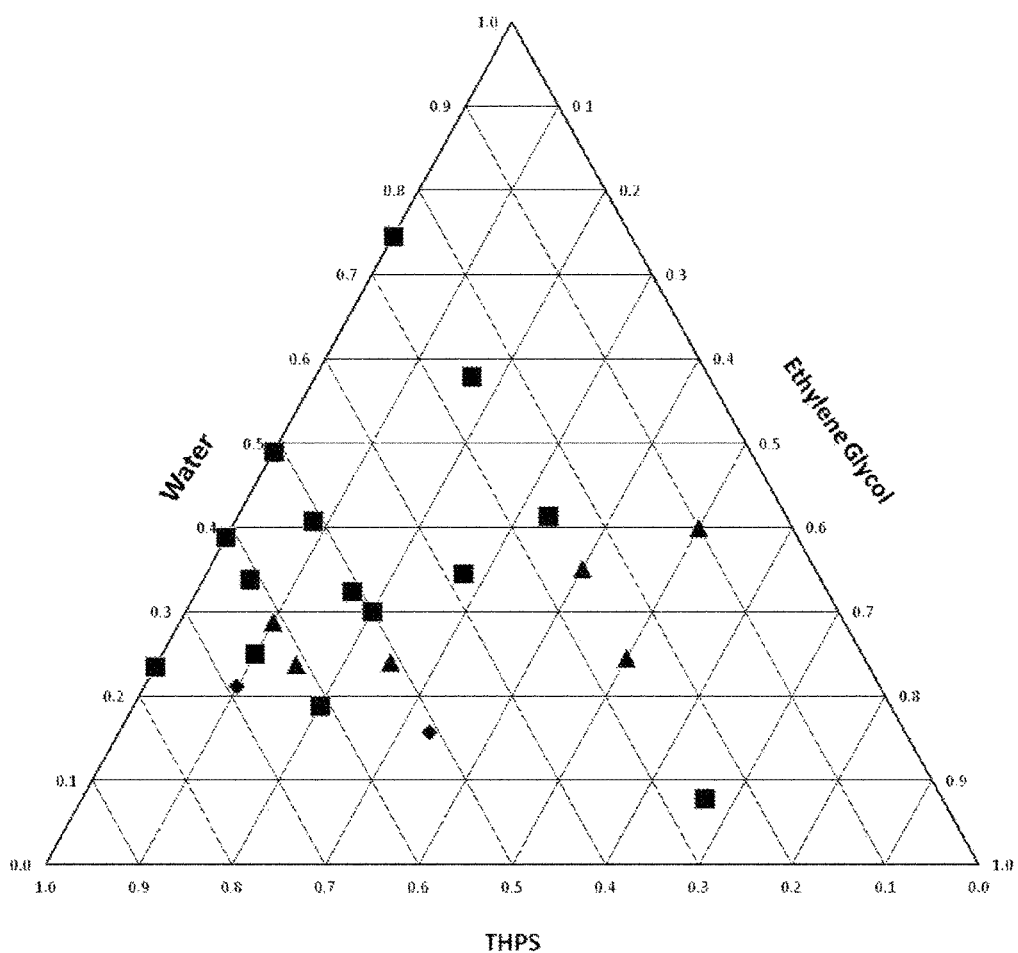
FIG. 2 is a ternary phase diagram for THPS/water/ethylene glycol. The symbols are the same as those indicated for FIG. 1.
Figure 3:
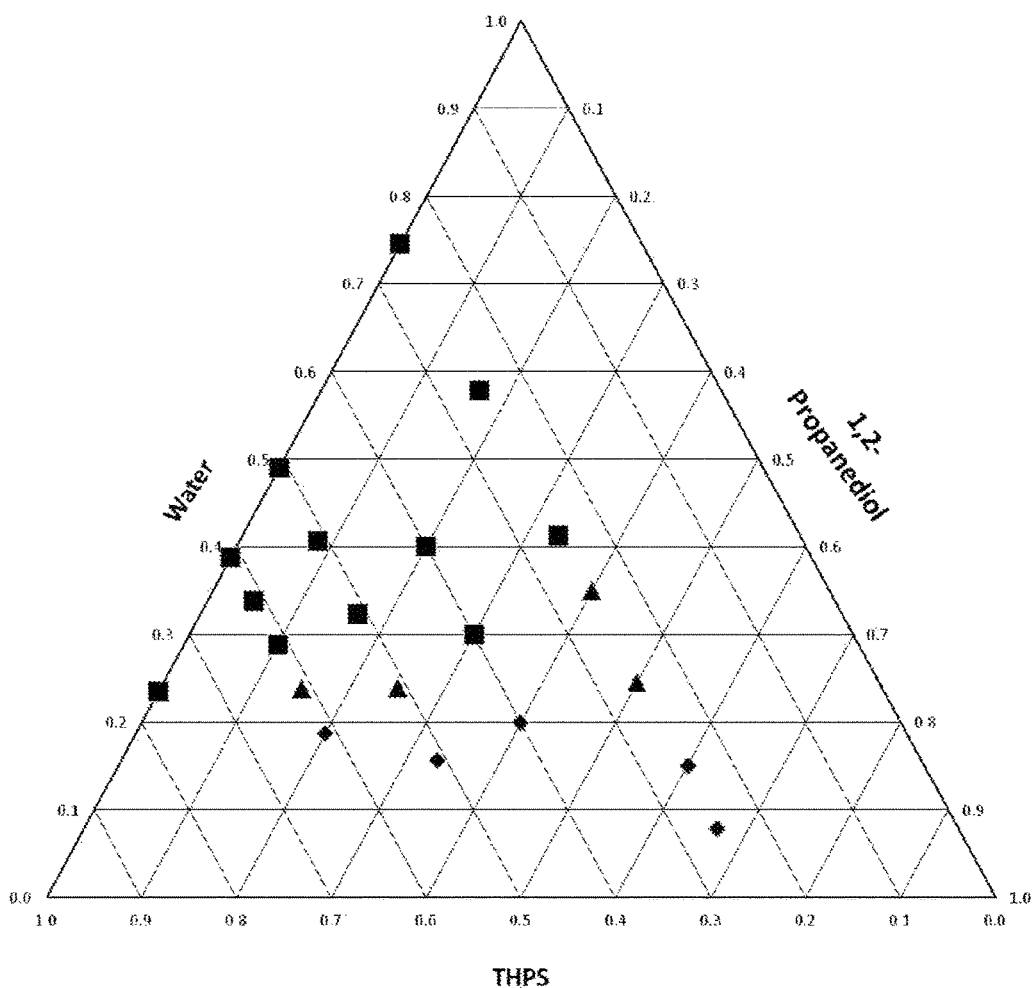
FIG. 3 is a ternary phase diagram for THPS/water/propylene glycol. The symbols are the same as those indicated for FIG. 1.
Figure 4:
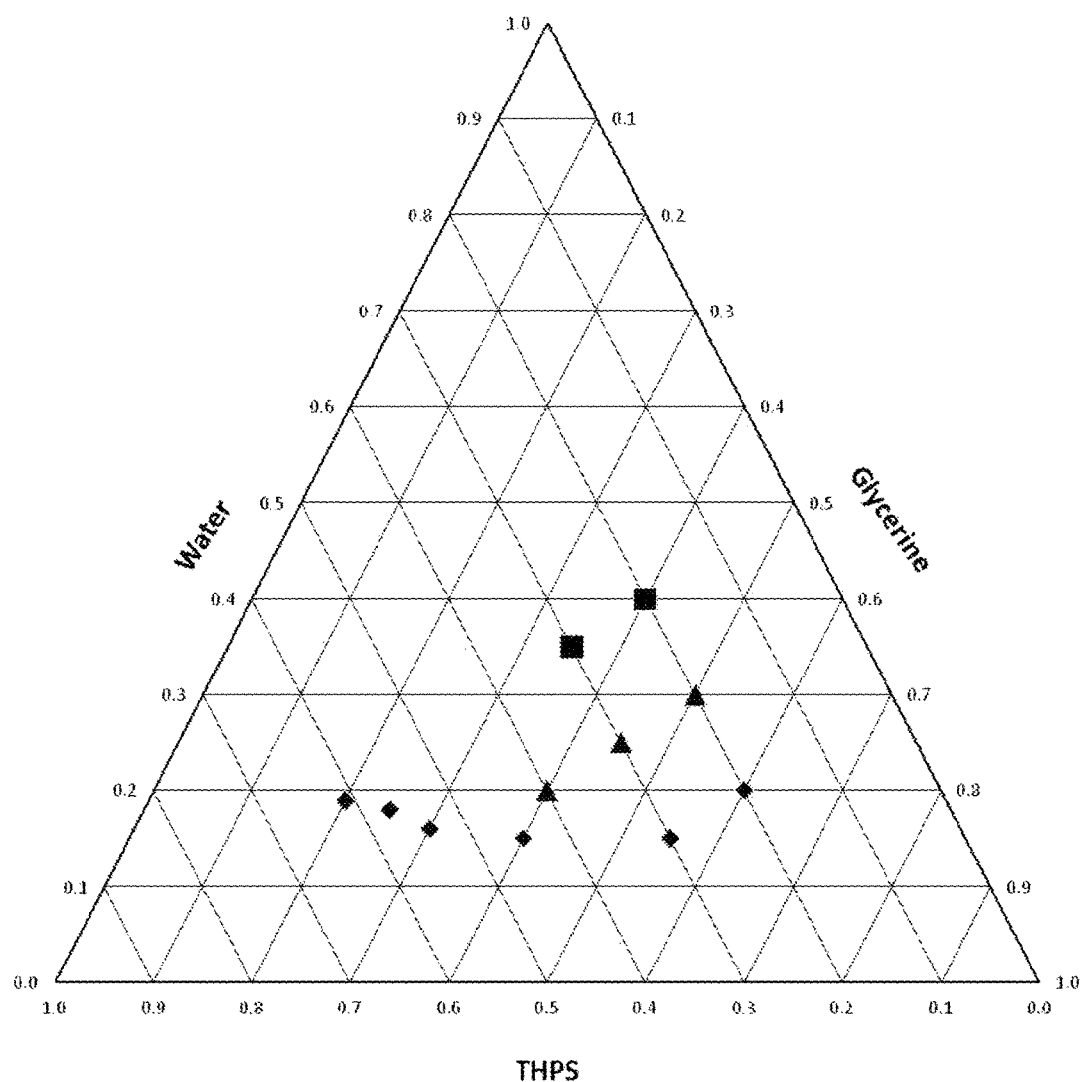
FIG. 4 is a ternary phase diagram for THPS/water/glycerine. The symbols are the same as those indicated for FIG. 1.

Unless otherwise specified, temperatures are in degrees centigrade (° C.), and references to percentages are by weight (wt %). All operations were performed at room temperature (20-25° C.), unless otherwise specified.

Compositions within the scope of this invention are those for which the weight percentages of (a), (b) and (c) are within the triangle defined by the three points, A, B and C listed above on a ternary phase diagram for THPS, water and methanol. In one preferred embodiment of the invention, the composition is within the area defined by the points: (E) 9% THPS/56% water/35% methanol; (F) 9% THPS/36% water/55% methanol; (G) 65% THPS/27% water/8% methanol; and (H) 65% THPS/29% water/6% methanol. The composition may contain small amounts of other ingredients, e.g., solvents, process impurities associated with the commercial active ingredient, surfactants, defoamer agents, dispersing agents, brand identification markers; preferably no more than 5 wt % of other ingredients, preferably no more than 4 wt %, preferably no more than 3 wt %, preferably no more than 2 wt %, preferably no more than 1 wt %, preferably no more than 0.5 wt %, preferably no more than 0.3 wt %. A composition containing other ingredients is evaluated by normalizing the total of the weight percentages of THPS, water and methanol to 100%; the composition is within the scope of the present invention if the point on a ternary phase diagram representing these normalized amounts is within the stated area.

In one preferred embodiment of the invention, the composition is within the area defined by the points: (I) 25% THPS/48% water/27% methanol; (J) 25% THPS/33% water/42% methanol; (K) 65% THPS/27% water/8% methanol and (L) 65% THPS/29% water/6% methanol; preferably (M) 35% THPS/43% water/22% methanol; (N) 35% THPS/32% water/33% methanol; (O) 65% THPS/27% water/8% methanol; and (P) 65% THPS/29% water/6% methanol.

The composition of the present invention is a free-flowing liquid even after storage at −40° C. Known aqueous solutions of THPS are not physically stable under these conditions. The prior art provided no indication that one could make a solution of THPS that would not freeze or phase-separate at −40° C.

EXAMPLES

Example 1

To a glass sample vial was added: (i) commercial aqueous solution of bis[tetrakis(hydroxymethyl)phosphonium] sulfate containing 76.5 wt % THPS and (ii) water, or an alcohol selected from methanol, ethanol or isopropanol (IPA), or a combination of water and one of the listed alcohols in an amount sufficient to produce a 20 g sample. Each sample was then placed in a −40° C. freezer. The samples were observed after 24 hours and the physical form was noted in Table 1. Reexamination of the samples after several days revealed them to be unchanged from the original observation. Only those samples diluted with a combination of water and methanol appeared as free flowing homogeneous liquids.

TABLE 1

Impact of Alcohol Diluents

| Sample | THPS | Water | Alcohol | MeOH | EtOH | IPA |
|---|---|---|---|---|---|---|
| control | 76.5% | 23.5% | 0.0% | Frozen | Frozen | Frozen |
| water only | 61.2% | 38.8% | 0.0% | Frozen | Frozen | Frozen |
| water only | 51.0% | 49.0% | 0.0% | Frozen | Frozen | Frozen |

TABLE 1-continued

Impact of Alcohol Diluents

| Sample | THPS | Water | Alcohol | MeOH | EtOH | IPA |
|---|---|---|---|---|---|---|
| water only | 25.5% | 74.5% | 0.0% | Frozen | Frozen | Frozen |
| Alcohol Only | 61.2% | 18.8% | 20.0% | small bi-layer liquid | bi-layer liquid | bi-layer liquid |
| Alcohol Only | 51.0% | 15.7% | 33.3% | bi-layer liquid | bi-layer liquid | bi-layer liquid |
| Alcohol Only | 25.5% | 7.8% | 66.7% | bi-layer liquid/solid | bi-layer liquid | bi-layer liquid |
| Equal Blend | 61.2% | 28.8% | 10.0% | Free flowing liquid | Frozen | Frozen |
| Equal Blend | 51.0% | 32.3% | 16.7% | Free flowing liquid | Frozen | Frozen |
| Equal Blend | 25.5% | 41.2% | 33.3% | Free flowing liquid | Frozen | Frozen |
| Low Alcohol | 61.2% | 33.8% | 5.0% | Frozen | Frozen | Frozen |
| Low Alcohol | 51.0% | 40.7% | 8.3% | Frozen | Frozen | Frozen |
| Low Alcohol | 25.5% | 57.8% | 16.7% | Frozen | Frozen | Frozen |
| High Alcohol | 61.2% | 23.8% | 15.0% | bi-layer liquid | bi-layer liquid | bi-layer liquid/solid |
| High Alcohol | 51.0% | 24.0% | 25.0% | bi-layer liquid | bi-layer liquid | bi-layer liquid/solid |
| High Alcohol | 25.5% | 24.5% | 50.0% | bi-layer liquid | bi-layer liquid | bi-layer liquid/solid |

Example 2

To a glass sample vial was added commercial solution of bis[tetrakis(hydroxymethyl)phosphonium] sulfate solution, water and methanol in an amount sufficient to produce a 20 g sample. The composition of each sample is shown below in table 2. Each sample was then placed in a −40° C. freezer. The samples were observed after 24 hours and the physical form was noted in Table 2. Reexamination of the samples after several days revealed them to be unchanged from the original observation.

TABLE 2

| THPS | Water | Methanol | Condition |
|---|---|---|---|
| 10% | 10% | 80% | Free flowing liquid |
| 10.0% | 20.0% | 70.0% | Free flowing liquid |
| 10.0% | 25.0% | 65.0% | Free flowing liquid |
| 10.0% | 35.0% | 55.0% | Free flowing liquid |
| 10.0% | 45.0% | 45.0% | Free flowing liquid |
| 10.0% | 55.0% | 35.0% | Free flowing liquid |
| 10.0% | 60.0% | 30.0% | Frozen |
| 10.0% | 70.0% | 20.0% | Frozen |
| 15% | 25% | 60% | Free flowing liquid |
| 20.0% | 20.0% | 60.0% | Bi-layer liquid |
| 20.0% | 30.0% | 50.0% | Bi-layer liquid |
| 25.0% | 30.0% | 45.0% | bi-layer liquid |
| 25.0% | 32.5% | 42.5% | Free flowing liquid |
| 25.0% | 35.0% | 40.0% | Free flowing liquid |
| 25.0% | 45.0% | 30.0% | Free flowing liquid |
| 25.0% | 48.0% | 27.0% | Free flowing liquid |
| 25.0% | 50.0% | 25.0% | Frozen |
| 25.5% | 7.8% | 66.7% | bi-layer liquid/solid |
| 25.5% | 24.5% | 50.0% | bi-layer liquid |
| 25.5% | 41.2% | 33.3% | Free flowing liquid |
| 25.5% | 57.8% | 16.7% | Frozen |
| 25.5% | 74.5% | 0.0% | Frozen |
| 30.0% | 30.0% | 40.0% | Bi-layer liquid |
| 30.0% | 35.0% | 35.0% | Bi-layer liquid |
| 30% | 35% | 35% | Free flowing liquid |
| 30.0% | 42.5% | 27.5% | Free flowing liquid |
| 30.0% | 47.0% | 23.0% | Frozen |
| 30.0% | 57.0% | 13.0% | Frozen |
| 40.0% | 30.0% | 30.0% | bi-layer liquid |
| 40.0% | 33.0% | 27.0% | Free flowing liquid |
| 40.0% | 40.0% | 20.0% | Free flowing liquid |
| 40.0% | 42.0% | 18.0% | Free flowing liquid |
| 40% | 45% | 15% | Frozen |
| 50.0% | 37.0% | 13.0% | Frozen |
| 50.0% | 28% | 22% | Free flowing liquid |
| 51.0% | 15.7% | 33.3% | bi-layer liquid |
| 51.0% | 24.0% | 25.0% | bi-layer liquid |
| 51.0% | 32.3% | 16.7% | Free flowing liquid |
| 51.0% | 40.7% | 8.3% | Frozen |
| 51.0% | 49.0% | 0.0% | Frozen |
| 60% | 27% | 13% | Free flowing liquid |
| 61.2% | 18.8% | 20.0% | small bi-layer liquid |
| 61.2% | 23.8% | 15.0% | bi-layer liquid |
| 61.2% | 28.8% | 10.0% | Free flowing liquid |
| 61.2% | 30.8% | 8.0% | Free flowing liquid |
| 61.2% | 33.8% | 5.0% | Frozen |
| 61.2% | 38.8% | 0.0% | Frozen |
| 70.0% | 25.0% | 5.0% | Frozen |
| 76.5% | 23.5% | 0.0% | Frozen |

Example 3. (Comparative)

To a glass sample vial was added commercial solution of bis[tetrakis(hydroxymethyl)phosphonium] sulfate solution, water and ethylene glycol in an amount sufficient to produce a 20 g sample. The composition of each sample is shown below in Table 3. Each sample was then placed in a −40° C. freezer. The samples were observed after 24 hours and the physical form was noted in Table 3. Reexamination of the samples after several days revealed them to be unchanged from the original observation.

TABLE 3

Ethylene Glycol.

| THPS | Water | Ethylene Glycol | Condition |
|---|---|---|---|
| 10.0% | 40.0% | 50.0% | Liquid |
| 25.0% | 35.0% | 40.0% | Liquid |
| 25.5% | 7.8% | 66.7% | Frozen |
| 25.5% | 24.5% | 50.0% | Slightly Viscous Liquid |
| 25.5% | 41.2% | 33.3% | Frozen |
| 25.5% | 57.8% | 16.7% | Frozen |
| 25.5% | 74.5% | 0.0% | Frozen |
| 38.0% | 34.5% | 27.5% | Partially Frozen |
| 50.0% | 30.0% | 20.0% | Partially Frozen |
| 51.0% | 15.7% | 33.3% | Slightly Viscous Liquid |
| 51.0% | 24.0% | 25.0% | Slightly Viscous Liquid |
| 51.0% | 32.3% | 16.7% | Frozen |
| 51.0% | 40.7% | 8.3% | Frozen |
| 51.0% | 49.0% | 0.0% | Frozen |
| 61.2% | 18.8% | 20.0% | Frozen |
| 61.2% | 23.8% | 15.0% | Slightly Viscous Liquid |
| 61.2% | 28.8% | 10.0% | Frozen |
| 61.2% | 33.8% | 5.0% | Frozen |
| 61.2% | 38.8% | 0.0% | Frozen |
| 65.0% | 25.0% | 10.0% | Partially Frozen |
| 68.9% | 21.2% | 10.0% | Viscous Liquid |
| 76.5% | 23.5% | 0.0% | Frozen |

Example 4. (Comparative)

To a glass sample vial was added commercial solution of bis[tetrakis(hydroxymethyl)phosphonium] sulfate solution, water and propylene glycol in an amount sufficient to produce a 20 g sample. The composition of each sample is shown below in Table 4. Each sample was then placed in a −40° C. freezer. The samples were observed after 24 hours and the physical form was noted in Table 4. Reexamination of the samples after several days revealed them to be unchanged from the original observation.

TABLE 4

Propylene Glycol.

| THPS | Water | Propylene Glycol | Condition |
|---|---|---|---|
| 25% | 15% | 60% | Very Viscous |
| 25% | 35% | 40% | Slightly viscous liquid |
| 25.5% | 7.8% | 66.7% | Very viscous liquid |
| 25.5% | 24.5% | 50.0% | Slightly viscous liquid |
| 25.5% | 41.2% | 33.3% | Frozen |
| 25.5% | 57.8% | 16.7% | Frozen |
| 25.5% | 74.5% | 0.0% | Frozen |
| 40% | 20% | 40% | Very viscous liquid |
| 40% | 30% | 30% | Frozen |
| 40% | 40% | 20% | Frozen |
| 51.0% | 15.7% | 33.3% | Very viscous liquid |
| 51.0% | 24.0% | 25.0% | Slightly viscous liquid |
| 51.0% | 32.3% | 16.7% | Frozen |
| 51.0% | 40.7% | 8.3% | Frozen |
| 51.0% | 49.0% | 0.0% | Frozen |
| 61.2% | 18.8% | 20.0% | Very viscous liquid |
| 61.2% | 23.8% | 15.0% | Slightly viscous liquid |
| 61.2% | 28.8% | 10.0% | Frozen |
| 61.2% | 33.8% | 5.0% | Frozen |
| 61.2% | 38.8% | 0.0% | Frozen |
| 76.5% | 23.5% | 0.0% | Frozen |

Example 5. (Comparative)

To a glass sample vial was added commercial solution of bis[tetrakis(hydroxymethyl)phosphonium] sulfate solution, water and glycerine in an amount sufficient to produce a 20 g sample. The composition of each sample is shown below in table 2. Each sample was then placed in a −40° C. freezer. The samples were observed after 24 hours and the physical form was noted in table 1. Reexamination of the samples after several days revealed them to be unchanged from the original observation.

TABLE 5

Glycerin.

| THPS | Water | Glycerine | Condition |
|---|---|---|---|
| 20% | 20% | 60% | Very viscous liquid |
| 20% | 30% | 50% | Slightly viscous liquid |
| 20% | 40% | 40% | Frozen |
| 30% | 15% | 55% | Very viscous liquid |
| 30% | 25% | 45% | Viscous liquid |
| 30% | 35% | 35% | Frozen |
| 40% | 20% | 40% | Viscous liquid |
| 45% | 15% | 40% | Very Very viscous liquid |
| 54% | 16% | 30% | Very viscous liquid |
| 57% | 18% | 25% | Very viscous liquid |
| 61% | 19% | 20% | Viscous liquid |

The invention claimed is:

1. A composition comprising:
(a) tetrakis(hydroxymethyl)phosphonium sulfate (THPS); (b) water; and (c) methanol; wherein the weight percentages of (a), (b) and (c), normalized to total 100%, are within an area on a ternary phase diagram bounded by four points: (A) 5% THPS/58% water/37% methanol; (B) 5% THPS/36% water/59% methanol; (C) 65% THPS/27% water/8% methanol; and (D) 65% THPS/29% water/6% methanol; wherein the composition comprises no more than 5 wt % of substances other than (a), (b) and (c).

2. The composition of claim 1 in which the area is defined by points: (E) 9% THPS/57% water/34% methanol; (F) 9% THPS/34% water/57% methanol; (G) 65% THPS/27% water/8% methanol; and (H) 65% THPS/29% water/6% methanol.

3. The composition of claim 1 in which the composition comprises no more than 1 wt % of substances other than (a), (b) and (c).

4. A composition comprising about 50% THPS/28% water/22% methanol.

* * * * *